United States Patent [19]
Garfield et al.

[11] Patent Number: 5,991,649
[45] Date of Patent: *Nov. 23, 1999

[54] METHODS FOR ACTIVATING THE MUSCLE CELLS OR NERVES OF THE UTERUS OR CERVIX

[75] Inventors: Robert A. Garfield, Friendswood, Tex.; Krzysztof Chwalisz, Berlin, Germany

[73] Assignee: University of Texas, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/658,108

[22] Filed: Jun. 4, 1996

Related U.S. Application Data

[60] Continuation-in-part of application No. 08/386,674, Feb. 10, 1995, Pat. No. 5,522,877, which is a division of application No. 07/995,180, Dec. 22, 1992, Pat. No. 5,397,344.

[51] Int. Cl.⁶ ........................................................... A61B 5/04
[52] U.S. Cl. .................................. 600/372; 607/138
[58] Field of Search ..................... 128/421, 642, 128/733, 734; 607/39, 115, 116, 138; 600/372, 546, 547

[56] References Cited

U.S. PATENT DOCUMENTS

| | | |
|---|---|---|
| 2,924,213 | 2/1960 | Fleck . |
| 3,313,293 | 4/1967 | Chesebrough et al. . |
| 3,800,800 | 4/1974 | Garbe et al. ............................. 607/138 |
| 4,577,640 | 3/1986 | Hofmeister ............................. 128/738 |
| 4,630,611 | 12/1986 | King ...................................... 128/642 |
| 4,848,352 | 7/1989 | Pohndorf et al. ...................... 128/642 |
| 4,890,623 | 1/1990 | Cook et al. ............................. 128/642 |
| 4,967,761 | 11/1990 | Nathanielsz ............................. 128/733 |
| 5,184,619 | 2/1993 | Austin ..................................... 128/639 |
| 5,397,344 | 3/1995 | Garfield et al. ......................... 607/138 |
| 5,464,448 | 11/1995 | Malewicz ................................ 607/138 |
| 5,562,717 | 10/1996 | Tippey et al. ........................... 607/138 |
| 5,649,976 | 7/1997 | Malewicz ................................ 607/138 |

OTHER PUBLICATIONS

Miller et al., *American Physiological Society*, pp. C130–C141 (1989).
Garfield et al., *Science*, vol. 198, pp. 958–960 (Dec. 2, 1977).
Garfield et al., *In Vitro Toxicology*, vol. 3, No. 1, pp. 41–59 (1990).
Chwalisz et al., *Am. J. Obstet. Gynecol.*, vol. 165, No. 6, Part I, pp. 1760–1770 (Dec. 1991).
Garfield, *The Onset of Labor: Cellular & Integrative Mechanisms*, pp. 55–79 (1988).
Garfield et al., *Am. J. Obstet. Gynecol*, vol. 157, No. 5, pp. 1281–1285 (Nov. 1987).
Demianczuk et al., *Am. J. Obstet. Gynecol.*, vol. 149, No. 5, pp. 485–491 (Jul. 1, 1984).
Garfield, *Clinical Obstetrics and Gynecology*, vol. 27, No. 3, pp. 572–591 (Sep. 1984).
Puri et al., *Biology of Reproduction*, 27 967–957 (1982).
Garfield et al., *Am. J. Obstet. Gynecol*, vol. 142, No. 1, pp. 21–27 (Jan. 1, 1982).
Garfield et al., *Am. J. Obstet. Gynecol.*, vol. 140, No. 3, pp. 254–260 (Jun. 1, 1981).
Garfield et al., *Can. J. Physiol. Pharmacol.*, vol. 70, pp. 481–490 (1992).
Morizaki et al., *Am. J. Obstet. Gynecol.*, vol. 160, No. 1, pp. 218–228 (Jan. 1989).
Bulat et al., *Can. J. Physiol. Pharmacol.*, vol. 67, pp. 837–844 (1989).
Buchanan et al., *The Anatomical Record*, 221:611–618 (1988).

*Primary Examiner*—Max Hindenburg
*Attorney, Agent, or Firm*—Millen, White, Zelano & Branigan

[57] ABSTRACT

Muscle cells and nerves of the uterus and cervix are treated with electrical pulses having selective parameters in order to stimulate or inhibit contraction thereof. Either a needle or probe is provided having stimulation electrodes thereon from which the treatment pulses emanate. In a further embodiment, patients are simultaneously treated with pharmacological agents in conjunction with the electrical treatment.

31 Claims, 8 Drawing Sheets

METHODS FOR ACTIVATING THE MUSCLE CELLS OR NERVES OF THE UTERUS OR CERVIX

CROSS-REFERENCE TO RELATED APPLICATIONS

This application in a continuation-in-part of U.S. patent application Ser. No. 08/386,674, filed Feb. 10, 1995, now U.S. Pat. No. 5,522,877, issued Jun. 4, 1996, which is a divisional U.S. patent application Ser. No. 07/995,180, filed Dec. 22, 1992, now U.S. Pat. No. 5,397,344, issued Mar. 14, 1995.

BACKGROUND OF THE INVENTION

The invention relates to methods of and apparatus for activating the muscle cells or nerves of the uterus or cervix. More particularly, the invention relates to a method and instrument useful for stimulating or inhibiting uterine contractility for producing cervical ripening at the end of the period of gestation; and for regulating the uterus or cervix in non-pregnant patients.

Preterm labor is one of the major pathological states most frequently complicating pregnancy. Preterm birth is the major cause of prenatal morbidity and mortality (75%) and long term neurological handicaps. In spite of the use of different new tocolytics, the incidence of preterm labor and the incidence of prenatal morbidity and mortality has not changed over the last decades.

U.S. Pat. No. 5,397,344 and U.S. Pat. No. 5,522,877, both of which are incorporated herein by reference, address diagnosing labor (term and preterm) which is a significant problem faced by obstetricians. Preterm labor is the pathological state most frequently associated with this dilemma. Moreover, term labor often requires adjuvant therapy to halt or augment labor. Since there is spontaneous uterine activity during pregnancy, it is often not possible to distinguish between physiological uterine activity or preterm labor. The state of the cervix is commonly used as a predictor of preterm birth. However, the softening of the cervix, as well as the appearance of uterine contractions are relatively late in preterm labor.

Antiprogestins induce preparatory changes in the uterus in all stages of pregnancy. This results in the increase in myometrial responsiveness to oxytocic stimuli such as oxytocin or prostaglandins. The major effect of antiprogestins on the uterus is the preparation or conditioning of the myometrium to labor and delivery by inducing intercellular coupling which manifests itself by an increase in propagation due to an increase in gap junctions.

The uterus is quiescent throughout pregnancy to maintain a tranquil environment for the growing fetus. At the end of pregnancy normally the uterus beings to contract forcefully in a phasic manner (labor) to expel the fetus and other products of conceptions. Abnormally the uterus sometimes either begins to contract and labor prior to term (preterm labor) or fails to contract at term. Preterm labor occurs in about 10% of all pregnancies whereas the incidence of insufficient or absence of contractions at term is also very high (3 to 13%). In most cases the clinician is faced with the decision to either inhibit labor or stimulate it depending on the circumstances. However, the clinician has only subjective methods (state of cervix or number of contractions but not force of contraction) on which to base a decision.

The uterus is now known to pass through a series of steps prior to and during labor to prepare the muscle to contract in a coordinated, synchronous and therefore forceful manner. These steps include the development of gap junctions (low electrical resistance contacts), receptors and other events between and on the muscle cells that allow the uterus to contract as a syncytium and react to contractile agents. Contractions of the uterus are dependent upon electrical activity, therefore the presence of gap junctions is an important component of this process. These steps are known to be regulated by various physiological signals (hormones) and can be controlled pharmacologically. When the muscle cells pass through this state they become electrically and metabolically coupled. This state allows the uterus to contract forcefully and frequently. Although this process is known to occur during pregnancy, it also appears during the menstrual cycle and may be present in various pathological conditions of the uterus such as dysmenorrhea, endometriosis, habitual abortion, allergic reactions, etc. However, at present, the obstetrician or gynecologist has no objective method to evaluate this process and to intervene when necessary by activating muscle cells or nerves of the uterus or cervix. The clinical judgement as to treatment is enhanced by procedures which define the state of the patients uterus such as the procedures of U.S. Pat. No. 5,522,877 and U.S. Pat. No. 5,397,344. There are, however, no current procedures for using the concepts of these patents to stimulate or inhibit activity in order to treat patients have the aforementioned difficulties.

Numerous studies show that gap junctions are present in almost all cells and their presence and function has been associated with normal physiological control. Gap junctions are also known to be altered either structurally or functionally in pathological states such as cancer, hypoxia, inflammation, etc. Many studies demonstrate that one can assess gap junction presence or function by electrical simulation and recording of electrical events in adjacent cells.

There have been a number of studies with respect to this matter such as Miller, S. M., et al., "Improved Propagation in Myometrium Associated with Gap Junctions During Parturition", *American Journal of Physiology*, pages 130–141 (1989), incorporated herein by reference, in which gap junction measurements were made on uterine tissue of pregnant rats. Additional studies which are reported in the literature include: Garfield et al., "Modulation of Myometrial Gap Junctions: Toxicological Implications", *In Vitro Toxicology, A Journal of Molecular and Cellular Toxicology*, Vol. 3, Number 1, pp. 41–59 (1990); Chwalisz et al., "The Progesterone Antagonist Onapristone Increases the Effectiveness of Oxytocin to Produce Delivery without Changing the Myometrial Oxytocin Receptor Concentrations", *Am. J. Obstet. Gynecol*, Vol. 165, No. 6, Part 1, pp. 1760–1770 (December 1991); Garfield, "Structural and Functional Studies of the Control of Myometrial Contractility and Labor", *The Onset of Labor: Cellular & Integrative Mechanisms*, pp. 55–79 (1988); Garfield et al., "Effects of the Antiprogesterone RU 486 on Preterm Birth in the Rate", *American Journal of Obstetrics and Gynecology*, Vol. 157, No. 5, pp. 1281–1285 (November 1987); Demanczuk et al., "Myometrial Electrophysiologic Activity and Gap Junctions in the Pregnant Rabbit", *American Journal of Obstetrics and Gynecology*, Vol. 149, No. 5, pp. 485–491 (Jul. 1, 1984); Garfield, "Control of Myometrial Function in Preterm Versus Term Labor", *Clinical Obstetrics and Gynecology*, Vol. 27, No. 3, pp. 572–591 (September 1984); Puri et al., "Changes in Hormone Levels and Gap Junctions in the Rat Uterus During Pregnancy and Parturition", *Biology of Reproduction*, 27, 967–975 (1892); Garfield et al., "Endocrine, Structural, and Functional Changes in the Uterus During Premature Labor", *American Journal of Obstetrics and Gynecology*, Vol. 142, No. 1, pp. 21–27 (Jan. 1, 1982); Garfield et al., "Appearance of Gap Junctions in the Myometrium of Women During Labor", *American Journal of Obstetrics and Gynecology*, Vol. 140, No. 3, pp. 254–260 (Jun. 1, 1981); Garfield et al., "Presence of Gap Junctions in the Myometrium of Women During Various Stages of Menstruation", *American Journal of Obstetrics and Gynecology*, Vol. 138, No. 5, pp. 569–574 (Nov. 1, 1980); and Garfield et al., "Art Gap Junctions Necessary for Cell-to-Cell Coupling of Smooth Muscle?: An Update", *Can. J. Physiol. Pharmacol.*, Vol. 70, pp. 481–490 (1992); each of which is incorporated herein by reference. While these studies each recognize various aspects of the phenomenon of interest, they do not suggest just how one would utilize the phenomenon in practical medical procedure to electrically stimulate or inhibit activity of the uterus or cervix.

The status (function, location, Identification, etc.) of nerves and their terminals in tissues can be quantified also by selectively stimulating the nerves with electrical parameters that do not affect surrounding tissues. This so-called "field stimulation" has been used in many studies to activate nerves or their varicosities in tissues to assess, localize and identify nerves in tissues. Exemplary of such studies are the following articles: Garfield et al., "A Functional and Structural Study of the Innervation of the Human Uterus", *American Journal of Obstetrics and Gynecology*, Vol. 160, No. 1, pp. 218–228 (January 1989); Bulat et al., "Studies of the Innervation of Rabbit Myometrium and Cervix", *Can. J. Physiol. Pharmacol.*, Vol. 67, pp. 837844 (1989); and Buchanan et al., "Innervation and Gap Junction Formation in the Myometrium of Pregnant Little Brown Bats, *Myotis lucifugus*", *The Anatomical Record*, 221:611–618 (1988), each of which is incorporated herein by reference.

Prior methods and instruments for evaluating the status of the uterus have used external monitors which give little information of quantitative nature necessary to define the processes described above or to electrically stimulate or inhibit activity of the uterus or cervix.

SUMMARY OF THE INVENTION

A feature of the present method and invention is to electrically stimulate or inhibit electrical and mechanical activity of tissues, such as for example, but not limited to, uterine muscle tissue and tissue of the cervix.

Upon further study of the specification and appended claims, further features and advantages of this invention will become apparent to those skilled in the art.

The present method and apparatus is applicable to the wide range of obstetrical, gynecological and other conditions. One such application is to either activate either the muscle cells or nerves of the uterus or cervix during term and preterm labor. Another application is the nonpregnant uterus or cervix for regulating various treatments. The method and apparatus is also valuable for use in connection with other tissues other than the uterus such as tissues of the bladder, intestine, heart and other muscular or nonmuscular (brain, liver, pancreas, etc.) tissues for purposes of evaluating their normal and abnormal behavior. The method and instrument is also usable for stimulating or inhibiting tissues in animals, as for example in a veterinary clinic or for live stock.

In accordance with one specific aspect of the invention, a needle includes stimulating electrodes as well as optional miniature piezoelectric electrodes embedded along an inner surface thereof. In accordance with one embodiment, the needle is placed in the uterine wall (i.e., myometrium) under ultrasound guidance similar to routine procedures during amniotic fluid sampling. The signals from the needle provide electrically evoked activity. The needle is connected to a multichannel recorder, stimulator and computer with software for generation of the signals.

Alternative embodiments of the needle utilize electrodes mounted on the exterior thereof.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
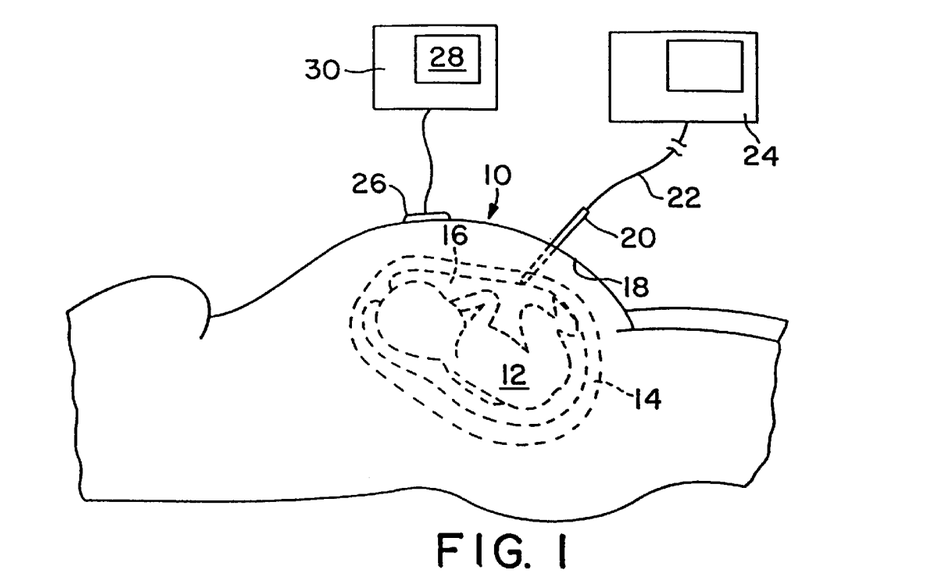
FIG. 1 is a side view, partially in phantom, showing a needle configured in accordance with the instant invention inserted in the uterine wall of a pregnant patient, the needle being connected to a recording device and the position of the needle being monitored by an ultrasonic scanner.

Referring now to FIG. 1, there is shown schematically a pregnant patient 10 with a fetus 12 retained with a uterine wall 14 which defines an amniotic cavity 16 having amniotic fluid therein. The uterine wall 14 is primarily configured of muscle tissue and is disposed proximate the abdominal wall 18 of the patient 10. In accordance with the principles of the instant invention, a needle 20 is passed from the exterior of the patient 10 through the abdominal wall 18 and embedded in the uterine wall 14. The needle has a bundle of leads 22 which are connected to a recording apparatus 24.

In accordance with the principles of the instant invention, the uterus of the pregnant patient 10 is monitored by ultrasonic transducers 26 to provide an image 28 of the uterine wall on an ultrasonic monitor 30 so that the shank 31 of the needle 20 may be accurately guided and properly embedded in the uterine wall 14.

Figure 2:
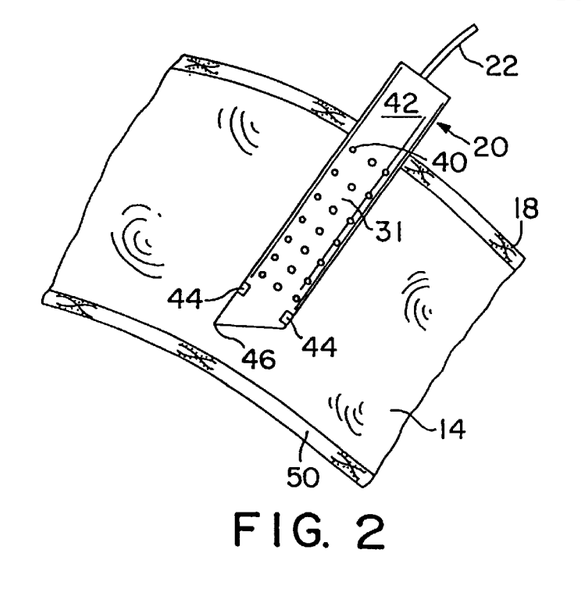
FIG. 2 is an enlarged, side elevational view illustrating the needle of FIG. 1 embedded in the muscle tissue of the uterine wall.

Referring now to FIG. 2, a greatly enlarged view of a section of uterine wall 14 is shown with the shank 31 of the needle 20 embedded therein after having been passed through the abdominal wall 18. The needle 20 is preferably made of stainless steel and has an overall length of about 65 mm. An array of recording electrodes 40 are disposed on the cylindrical surface 42 of the needle 20 and an array of stimulation electrodes 44 are positioned proximate the tip 46 of the needle. The arrays of recording and stimulation electrodes 40 and 44 are completely embedded in the muscle tissue of the uterine wall 14 with the muscle tissue extending into the hollow core of the needle. In accordance with one embodiment of the invention, the tip 46 of the needle 20 does not penetrate the endometrium 50 which is disposed between the muscle 14 of the uterine wall and the amniotic fluid 16. In accordance with another embodiment of the invention, the needle 20 is a hollow amniotic fluid sampling needle which performs fluid sampling alternative to electrical monitoring.

Figure 3:
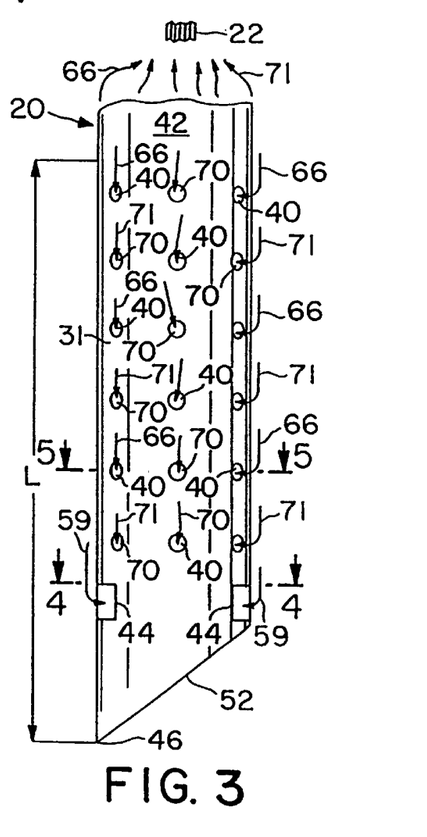
FIG. 3 is a further enlarged side view showing a portion of the exterior surface of the needle shown in FIGS. 1 and 2.

Referring now to FIG. 3, there is shown a side view of the needle 20 where it is seen that the embedded portion of the needle having the array of recording electrode 40 and stimulating electrodes 44 has a length L of about 2–4 mm and a diameter of about 0.5 to 2 mm. The recording electrode 40 are spaced from one another by a distance of about 0.5 mm, while the stimulation electrodes 44 are a height and width of about 0.5 mm. The tip 46 of the needle 20 is disposed approximately 0.5 mm from the bottom of the array of stimulation electrodes 44 and has a sloping edge 52 extending from one side of the needle to the tip 46 thereof. The dimensions defining spaces between various electrodes are suggested dimensions which may be varied from needle to needle to optimize performance of the needles 20.

Figure 4:
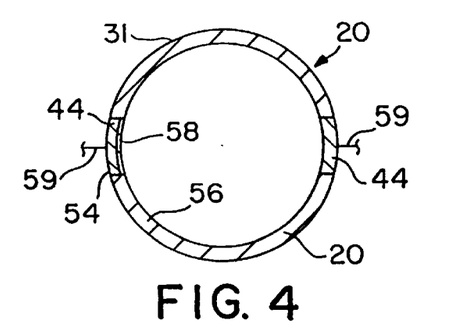
FIG. 4 is a sectional view taken along liens 4—4 of FIG. 3 showing an array of stimulation electrodes.

Referring now to FIG. 4, where the shank 31 of the needle 20 is shown in cross-section, the stimulation electrodes 44 are silver plated into indentations 54 of the wall 56 of the needle. The indentations 54 are first coated with an insulting material 58 to electrically isolate the stimulation electrodes 44 from the stainless steel needle shank 31. Each stimulation electrode 44 has an insulated lead 59 which is led back over the surface 42 of the needle 20 (see FIG. 3) into the lead bundle 22 and to the record device 24 (see FIG. 1). The stimulation electrodes 44 receive either depolarized or hyperpolarized current pulses from the recording device 24, with each pulse having a duration in the range of about 10 to 500 milliseconds, a frequency in the range of 0.05 to 5 Hz and an amplitude in the range of about 0.1 to 30 volts.

Figure 5:
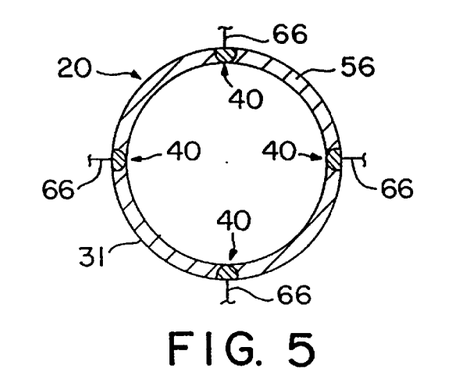
FIG. 5 is a cross-section view taken along lines 5—5 of FIG. 3 showing an array of recording electrodes.
Figure 6:
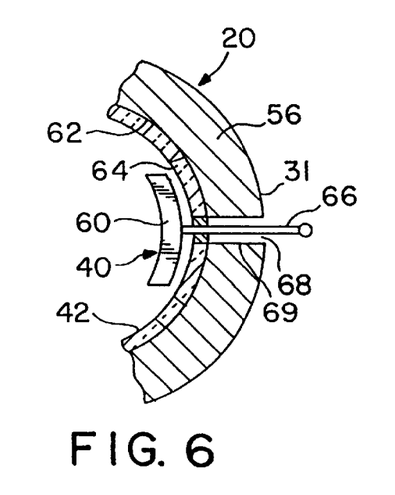
FIG. 6 is an enlarged sectional view of a portion of FIG. 5 showing how an individual recording electrode is mounted within the needle.

Referring now to FIGS. 5 and 6, there is shown the specific structure of one level of the array of recording electrodes 40 as well as the structure of a single recording electrode. In the illustrate embodiment, there are four recording electrodes disposed at 90° intervals around the wall 56 of the needle 20. As is seen in the specific embodiment of FIG. 6, each recording electrode 40 includes a plate 60 made of silver or another conductive material which is disposed inside of the needle 20 proximate the inner surface 62 of the wall 56. A layer of electrical insulation 64 is disposed between the plate 60 and the surface 62 of the wall 56 to electrically isolate the plate 60 from the stainless steel needle shank 31. An insulated lead 66 extends through a bore 68 through the wall of the needle 56 and a hole 69 in the insulation. As is seen in FIG. 1, the lead 66 from each recording electrode 40 extends back up in the needle and into the lead bundle 22 for connection to the recording apparatus 24. The silver plate 60 functions similar to an antenna and receiver signals generated in the muscle tissue 14 (see FIG. 2).

In an alternative apparatus, Instead of all the electrodes 40 being recording electrodes, the electrodes may be piezoelectric electrodes 70 which sense contractual events and transmit these events via insulated leads 71 to the recording apparatus 24. Preferably, the piezoelectric electrodes 70 are disposed between the recording electrodes to provide an alternating array as is shown in FIG. 3.

Figure 7:
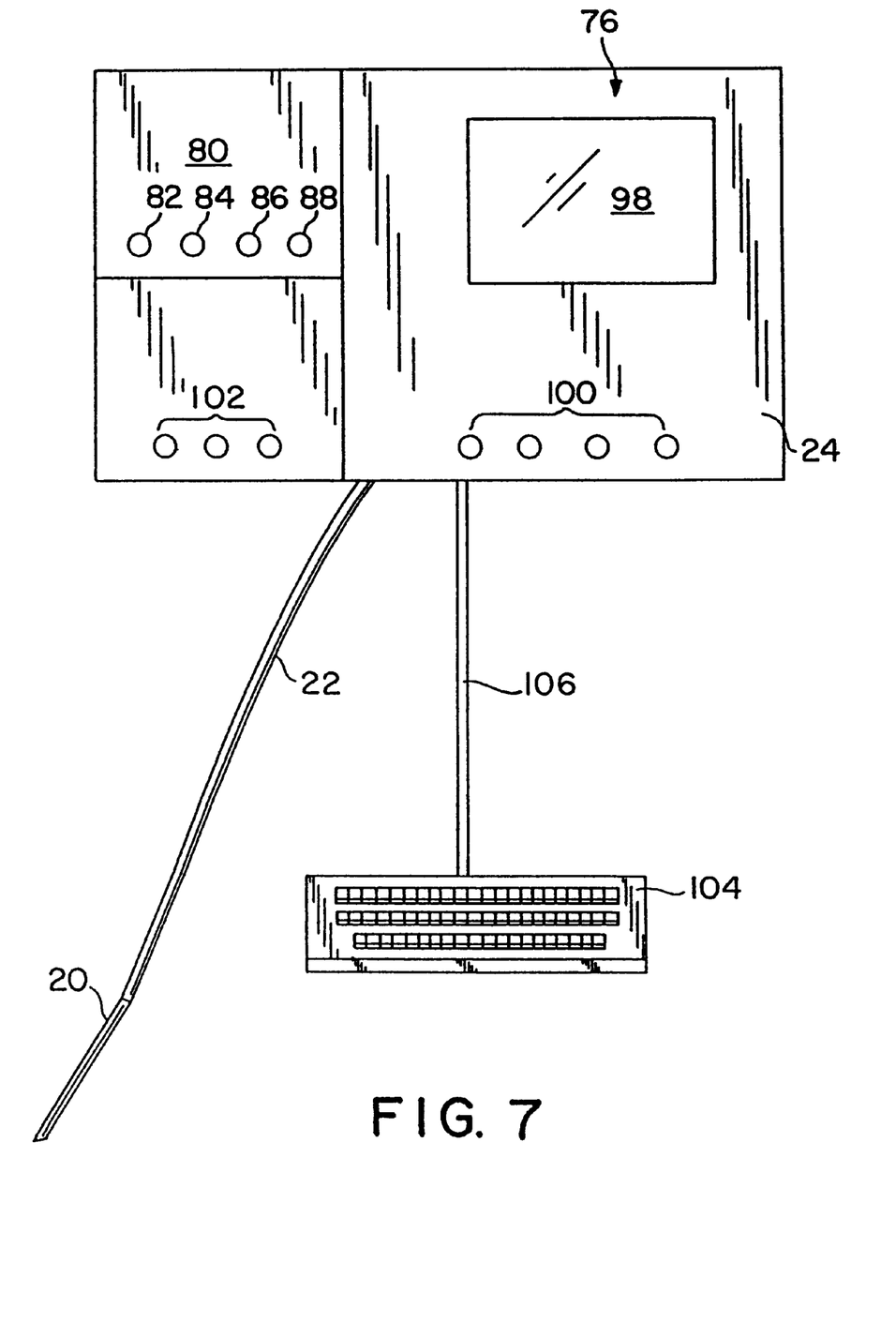
FIG. 7 is a front view of a typical recording apparatus to which the needle is connected and which provides stimulation signals and receives response signals.

Referring now to FIG. 7, where the recording apparatus 24 is shown, the recording apparatus includes a stimulator 80 for invoking electrical events in the needle 20. The stimulator 80 is of conventional design and includes a control for amplitude 82, a control for voltage 84, a control for duration 86 and a control for frequency 88. The stimulator is connected via cable bundle 22 to the stimulation electrodes 44 via leads 59. The recording apparatus 24 also includes a monitor 96 with a monitor screen 98 to display readings from the electrical leads 66 and 71 connected to the recording electrodes 40 and piezoelectric electrodes 70, respectively. In a conventional fashion, the monitor includes controls 100 for selecting various arrays for electrodes to be detected. For example, the controls may selected the recording electrodes 40 or the piezoelectric electrodes 70 for monitoring. Finally, recording apparatus 24 also includes controls 102 for amplifying and filtering the signals relayed over leads 41 and 71 to the monitor 96. A standard computer 104 is connected to the monitor 24 via cable 106. The computer 104 includes software and a key board for controlling the various functions of the recording apparatus 24

Figure 8:
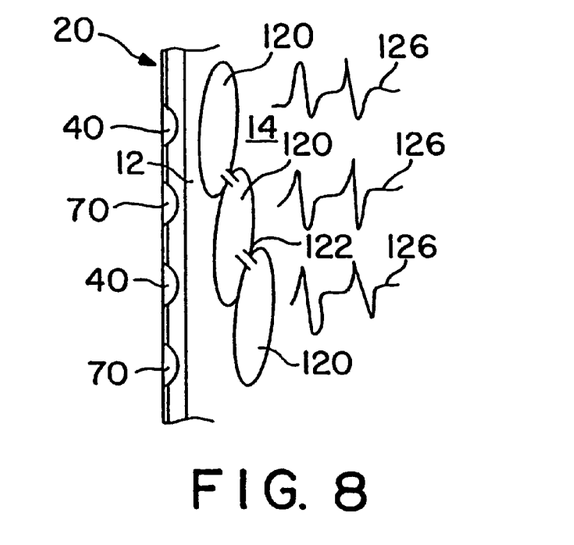
FIG. 8 is a schematic view of smooth muscle tissue in proximity with the needle of FIG. 1–7 illustrating the function of the instant invention.

Referring now to FIG. 8, it is seen that the needle 20 with the arrays of recording electrodes 40 and piezoelectric electrodes 70 are disposed proximate muscle cells 120 in the smooth muscle tissue of the uterine wall 14. Between each cell 120 and adjacent cells 120, there is schematically illustrated what is known as a gap junction 122 which is a low resistance electrical contact that develops prior to and during labor in order to prepare the smooth muscle tissue 14 for contraction in a coordinated and synchronous manner. Contractions of the uterine wall 14 are dependent upon propagation of electrical activity between the muscle cells; therefore, the presence of the gap junctions 122 is an important component of the contraction process. Gap junctions are known to be regulated by various physiological signals produced by hormones and can be controlled pharmacologically. When the muscle cells 120 contain open gap junctions, they become electrically and metabolically coupled which allows the uterus wall 44 to contract forcefully and frequently.

In accordance with the instant invention, the smooth muscle tissue 14 is stimulated with electrical pulses having parameters that affect only the cells 120 and not surrounding tissue. Monitoring is initiated by pulsing the stimulation electrodes 44 (FIGS. 2–4) with current pulses having a duration in the range of about 10 to 500 milliseconds at a frequency in the range of about 0.05 to 5 Hz and at a voltage amplitude in the range of about 0.1 to 30 volts. This stimulation causes spontaneous and electrically evoked action potentials 126 at the recording electrodes 40 as well mechanical interactions with the piezoelectric electrodes 70, which signals are transmitted over the leads 66 from the recording electrodes and leads 71 from the piezoelectric electrodes to the recording apparatus 24. In the recording apparatus 24, the amplifier 101 modulates the signals using a time constant of about 1 second at a high frequency filtration band pass in the range of 0.1 to 22 Hz. The thus monitored signals 126 are displayed on the monitor screen 98, then stored PC computer-based hardware and software in the computer 104 with a sampling range of about 500 digitized samples per second.

Figure 9:
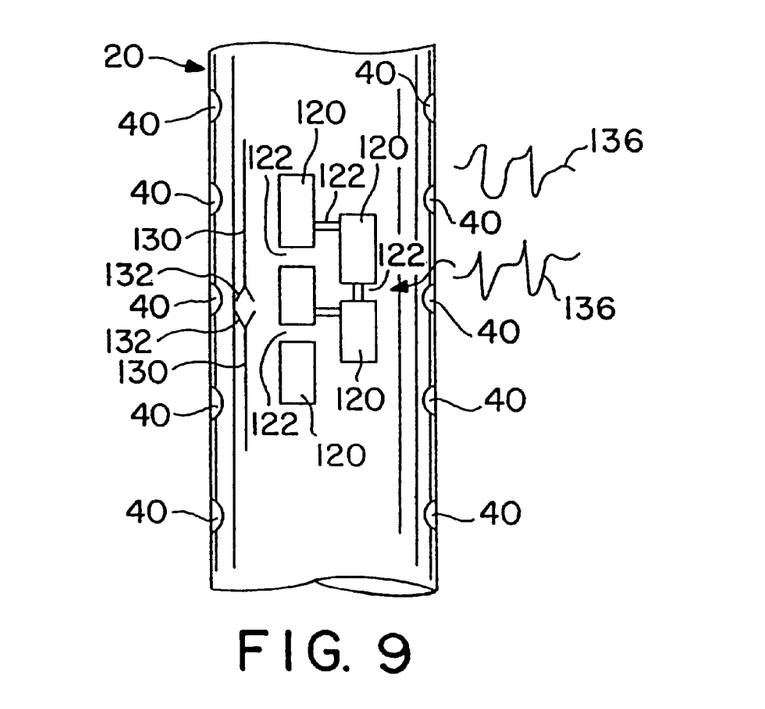
FIG. 9 is a view similar to FIG. 8 showing smooth muscle or other tissue with nerves proximate the needle of the instant invention and further illustrating an additional feature of the invention.

Referring now to FIG. 9, there is schematically shown the needle 12 and recording electrodes 40 in juxtaposition with cells 120 being in a state where there are gap junctions 122. Muscle tissue, which may be smooth muscle tissue or other muscle tissue, has peripheral nerves 130 therein with nerve endings 132. It is possible to stimulate nerves 130 and nerve endings 132 by pulsing the stimulation electrodes 44 (FIGS. 2, 3, 4) with parameters that do not activate the cells 120. The nerves 130 then act on the cells 120 and the cells generate signals 136 in the cells 120 which are detected by the electrodes 40. In this way, a physician is able to monitor the effects of nerve stimulation in isolation on the cells 120.

Referring now to FIG. 10–15, the recording apparatus 24 stores signals 126 in the associated computer 104 and extracts the following parameters derived from the signals 126:

a. duration of bursts of action potentials 126;

b. propagation velocity of individual action potentials in bursts following stimulation (measured from change in latency from successive electrodes 40);

c. patterns of propagation and distance of propagation during spontaneous and evoked action potentials;

d. entrainment of bursts.

e. velocity and distance of mechanical activity as measured by the piezoelectric electrodes 70;

f. characteristics of the contractions such as rate of rise and amplitude as detected by the piezoelectric electrodes; and g. characteristics of the action potentials such as the rate of rise of depolarization and plateau, amplitude and the rate of repolarization.

Figure 10:
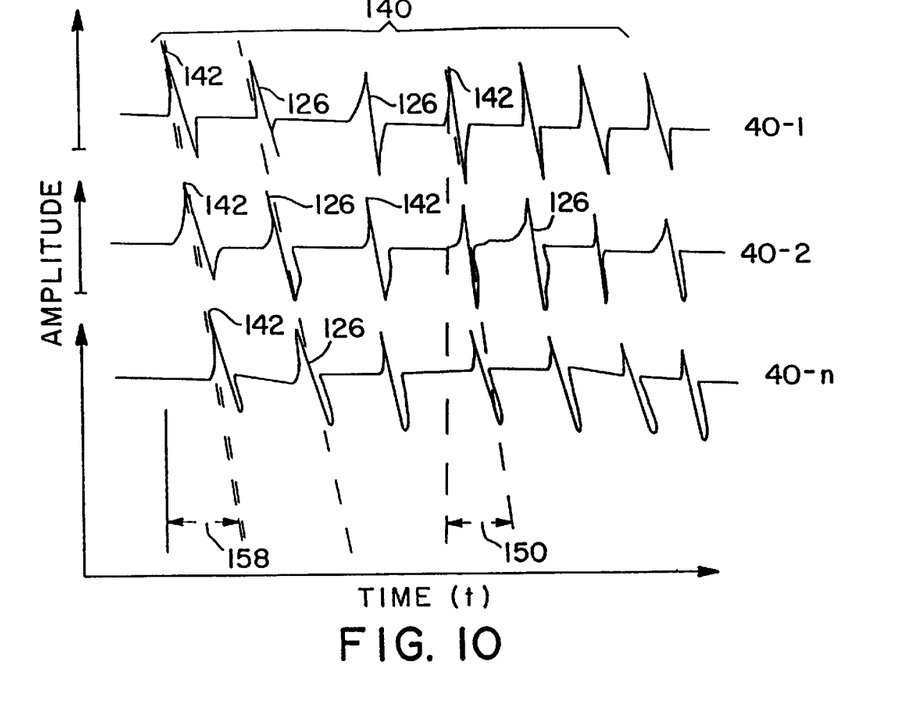
FIG. 10 is a diagrammatical view showing spontaneous electrical activity between cells detected by recording electrodes.

Considering the aforementioned parameters in more detail, as is seen in FIG. 10, the length of each burst 140 is plotted as a function of time t to provide the duration of each burst in seconds as detected by the electrodes 40-1 through 40-n. In addition, the computer 104 measures the action potential frequency in cycles per second by counting the number of spikes 142 per unit time.

Figure 11:
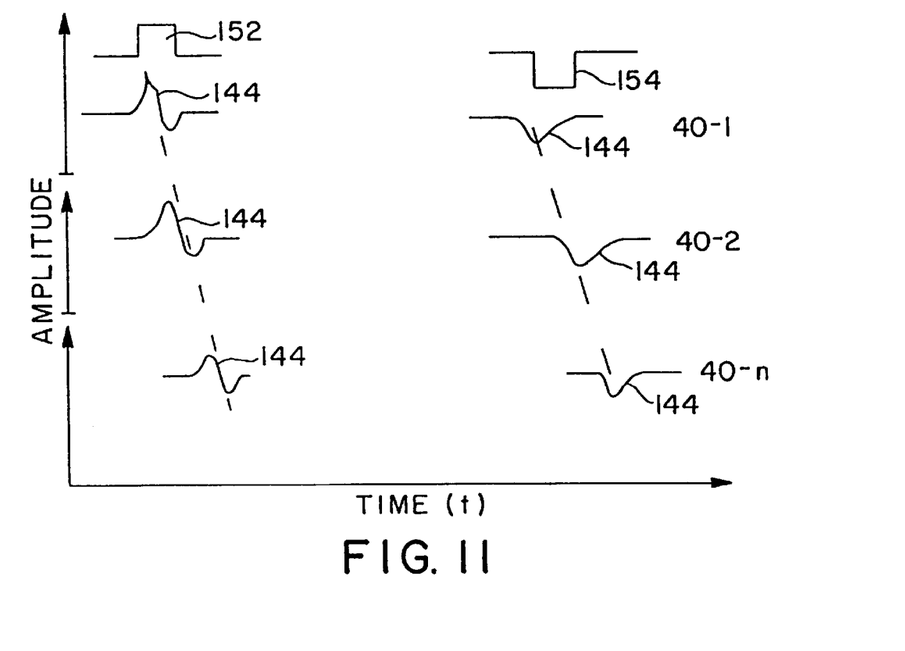
FIG. 11 is a diagrammatical view showing evoked electrical activity between cells.

The propagation obligation velocity of the individual action potentials 126 and evoked potentials 144 is seen from a consideration of FIGS. 10 and 11, wherein a latency period 150 between selective recording electrodes 40 is shown. In FIG. 11, the evoked electrical responses 126 from the electrodes 40 result from the application of a polarized pulse 152 or a hyperpolarized pulse 154 applied to the stimulation electrodes 44 (FIGS. 2, 3 and 4).

Figure 12:
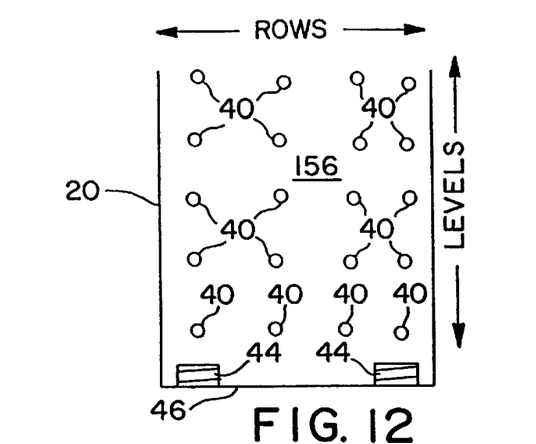
FIG. 12 is a linear diagram of an inner surface of the needle according to the instant invention with the recording electrodes arranged in a selected array.

Referring now to FIG. 12 in combination with FIGS. 10 and 11, a computer diagram of an array 156 of the electrodes 40 is shown with the electrodes arranged in levels and rows above the stimulation electrodes 44. The computer 104 computes the original and propagation characteristics of any of the bursts 140 shown in FIG. 10. Similarly, from stimulated potentials computer 104 calculates the propagation velocity in distance and displays this information on the screen 98 of the recording device 24. The entrainment of bursts 140 is seen by reference numeral 158 of FIG. 10 and is calculated from the initial latency period 160 between the bursts at each electrode 40.

Figure 13:
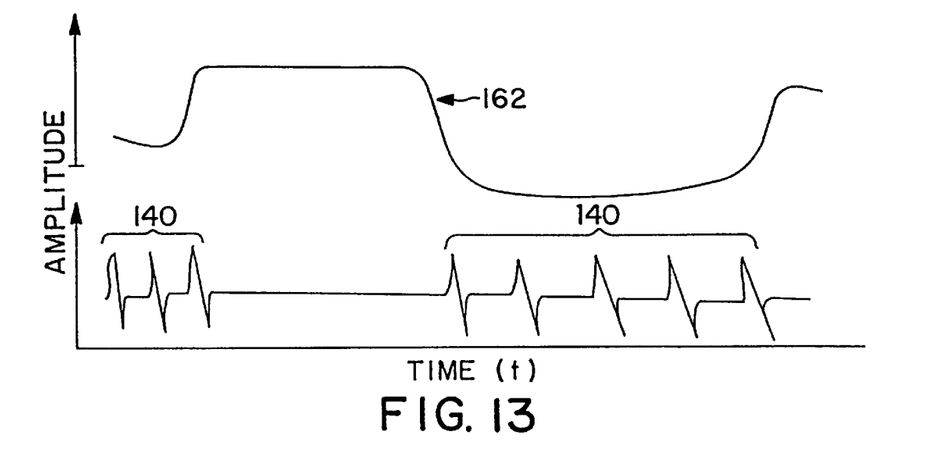
FIG. 13 is a diagrammatical view comprising cellular electrical activity in a muscle with muscle contractions.

Utilizing an approach similar to the approach for monitoring electrical activity, the computer 104 estimates the velocity and distance of the mechanical activity detected by the piezoelectrodes 70 (FIG. 3) which are indicative of the contractions of the uterine wall 14. As is seen in FIG. 13, the mechanical activity of muscle tissue comprising the uterus wall 14 is identified b a curve 162 which corresponds to the burst 140 indicative of the underlying electrical activity. Frequency, duration and magnetic of a contraction of the uterine wall 14 are respectively proportional to the frequency of the bursts 140, the duration of the bursts and the propagation of the action potential 126 to recruit additional cells 120 (see FIG. 8). The velocity of a contraction is estimated from the latency of contractions at successive piezoelectrodes 70 with the origin and distance of each contractual sequence being computed from a computer generated map of the needle 20 such as the map of FIG. 12 utilized for detecting action potentials 126.

Figure 14:
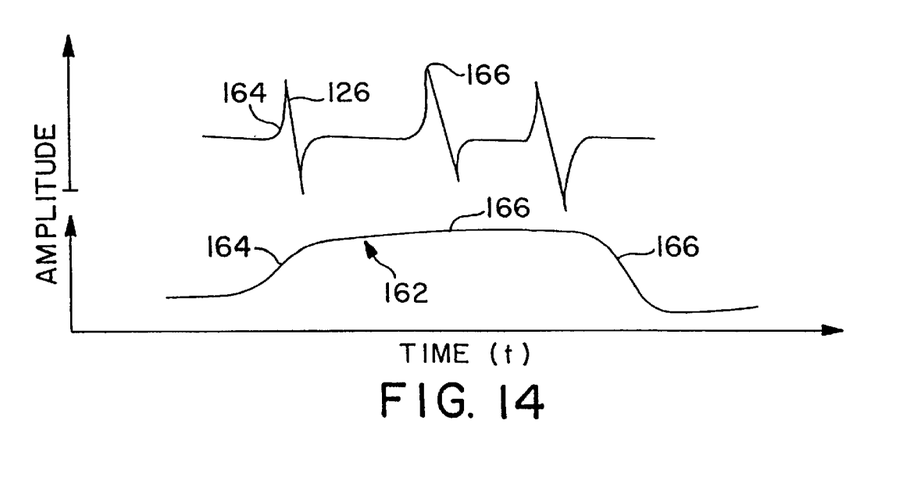
FIG. 14 is a diagrammatical view comparing cellular electrical activity and muscle contractions relating the rate of rise amplitude and the rates of depolarization and relaxation.

Referring now to FIG. 14, the characteristics of any contraction curve 162 or action potentials 126 contained in a burst 140 are isolated by the program of the computer 104. The rate of rise 164, amplitude 166, rate of repolarization and relaxation 166 can therefore be estimated.

From the aforedescribed measurements set forth in FIGS. 10–14, one can reasonably estimate if tissue, such as the muscle tissue of the uterine wall 14, or other tissue is coupled electrically. In other words, one can discern if the gap junctions 122 are present, absent or in a closed configuration. The presence of gap junctions 120 is generally indicative of the labor state for the uterine muscle comprising the uterine wall 14. On the other hand, the absence of electrical coupling suggests the ambience or closed state of the junctions and the lack of conditions favorable to labor.

While a preferred embodiment of the invention utilizes a signal needle 20 with both the stimulation electrodes 44 and the recording electrodes 40 thereon, in another embodiment of the invention, the stimulation electrodes 44 and recording electrodes 40 are on separate needles implanted at different locations. In another embodiment, the electrodes are mounted on the outside of the needle. In still another embodiment of the invention, the stimulation electrodes 44 are embedded in the tissue being monitored while the recording electrodes 40 are positioned outside that tissue on the patient's skin.

While utilization of the apparatus and method has been described above as especially useful for monitoring the uterine wall 14 during pregnancy, gap junctions 122 are present in almost all cells and the presence and function thereof is associated with normal physiological control. Gap junctions 122 are also known to be altered either structurally or functionally in pathological states such as cancer, hypoxia, inflammation and other pathological states. Accordingly, it is within the scope of this invention to utilize the apparatus and methods thereof for medical and biological procedures other than uterine wall monitoring.

Figure 15:
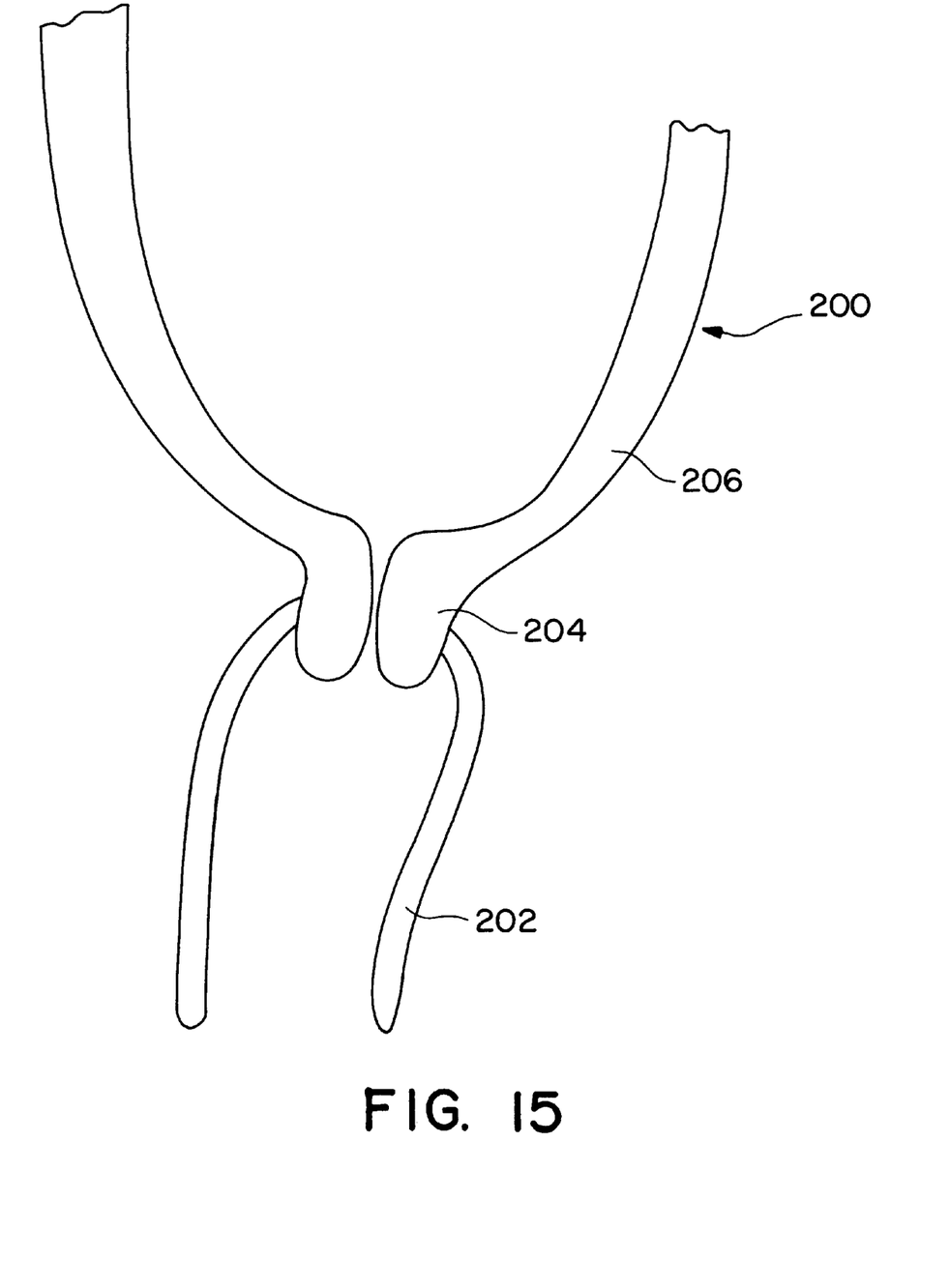
FIG. 15 is a side elevational view of the walls of human female genitalia including vaginal, cervical and uterine walls.
Figure 16:
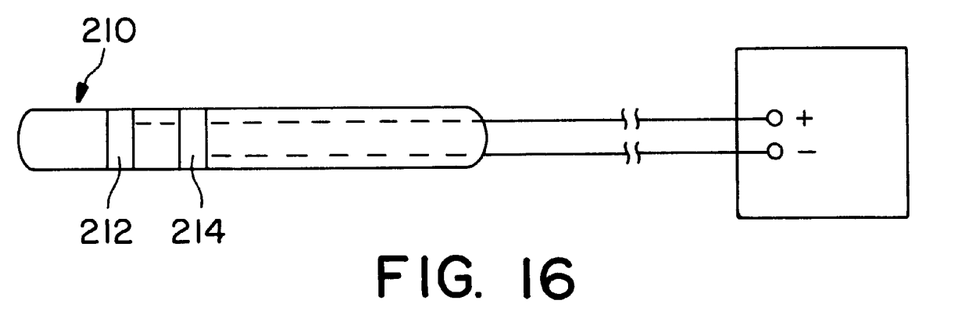
FIG. 16 is a probe configured in accordance with the principles of the present invention for stimulating or inhibiting contractual activity of the walls of FIG. 15.
Figure 17:
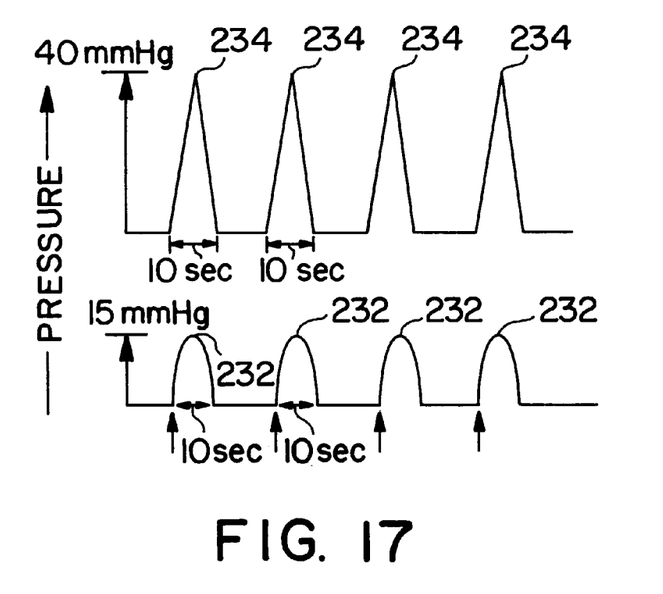
FIG. 17 is a diagrammatical view illustrating contractions of the cervix and uterus due to stimulation by the probe of FIG. 15.

FIGS. 15–17: Activating Muscle Cells or Nerves by Electrical Stimulation

Referring now to FIG. 15, walls of female genitalia are shown and include the vaginal wall 202, the cervical wall 204 and the uterine wall 206. In accordance with the present invention, a probe in the form of a needle, such as previously disclosed in this application, or a surface probe such as the probe of FIG. 16 utilize electrodes to activate either the muscle cells, such as the uterine cervix muscle cells 120 of FIG. 8, or the nerves 132 and nerve endings 130 of the uterus or cervix as is shown in FIG. 9. By varying stimulation parameters, either the muscle cells or nerves may be stimulated to either stimulate or inhibit uterine contractions or to stimulate or inhibit cervical dilation.

For stimulating or inhibiting muscle cells, signals having a duration in the range of 10 to 500 milliseconds at a frequency in the range of 0.05 to 5 Hz with a voltage in the range of 0.1 to 30 volts in trains in the range of 0.5 to 10 seconds are used. Preferred values for muscle applications are a duration of about 100 milliseconds at a frequency of about 1 Hz with a voltage of about 10 volts in trains of about 3 seconds. To stimulate the nerves, the duration of the pulses is 0.1 to 1 millisecond at a frequency of 2.5 to 60 Hz with a voltage of 10 to 80 volts in trains of 0.1 to 10 seconds. Preferred values for nerve applications are a duration of about 0.5 milliseconds at about 30 Hz with a voltage of about 50 volts in train of about 1 to 3 seconds.

This stimulation may be provided by either the needle structure of FIGS. 1–6 in which walls of the uterus, cervix or vagina are penetrated by a needle 20 or by a probe, such as the probe 210 of FIG. 16, which does not penetrate muscle tissue but applies electrical pulses through the surface of the vaginal, uterine or cervical walls with spaced electrodes such as the electrodes 212 and 214. The probe 210 is preferred since it is essentially non-evasive. Typically, the probe 210 would be about 0.5 mm in diameter and have a length of approximately 20 cm and is insertable into the vagina, cervix or uterus in order to stimulate the muscles or nerves thereof. The electrodes 212 and 214 are spaced about 1.0 cm apart and have a width of about 2 mm.

In accordance with the present invention, an electrical field created between the electrodes 212 and 214. When the electrodes are placed in contact with the walls adjacent muscle or nerve tissue, the field penetrates the tissue. The resulting stimulation (or inhibition) is therefore best described as "electrical field stimulation". Accordingly, by placing electrodes, such as the electrodes 212 and 214 on a probe 210, and inserting the probe into the uterus 206 or cervix 204 via the vaginal canal 202 one can selectively stimulate or inhibit muscle cells of the uterus or cervix. Moreover, the nerves in the uterus or cervix can be activated in a stimulatory or inhibitory fashion to either stimulate or inhibit contractibility of the uterus or cervix. Smooth muscle has a long chronaxie in the range of about 50 to 100 milliseconds so that electrical impulses of short duration in the range of about 0.6 milliseconds preferentially stimulate intramural nerve fibers. In this way, contractility of the uterus and cervix is electrically controlled by the probe 210 of FIG. 16 or the needle 20 of FIGS. 1–6 so as to regulate these organs by controlling the pace of muscle activity.

As is seen in FIG. 19, stimulation of the uterus or cervix results in contractions lasting approximately 10 seconds with pressure amplitude in the range of about 40 mmHg for the cervix and about 15 mmHg for the uterus after electrical stimulation occurring at points 230 prior to the rise of the peaks 232 for the uterus and 234 of the cervix. As is seen in FIG. 19, the pressure of the cervical contractions is approximately three times as large as the pressure of uterine contractions.

The primary use of this technology is for pregnant women to stimulate or inhibit uterine contractility and to produce cervical ripening which occurs at the end of gestation. These techniques are, however, also useful to treat non-pregnant patients in order to regulate the activity of the uterus or cervix.

By using the electrical stimulation described herein in combination with pharmacological agents such as prostaglandins, antiprogestins and oxytocins, cervical and uterine activity is stimulated. By applying electrical pulses described herein with nitric oxide, β-agonists and steroid hormones contractility of the uterus and cervix is inhibited. The pharmacological agents with which electrical stimulation or inhibition is utilized are the agents disclosed in the following patent applications incorporated herein by reference: Ser. No. 08/153,345, filed Nov. 16, 1993; Ser. No. 08/092,426, filed Jul. 16, 1993; Ser. No. 08/466,688, filed Jun. 6, 1995; Ser. No. 08/152,496, filed Nov. 16, 1993; Ser. No. 08/437,462, filed May 8, 1995; Ser. No. 08/254,584, filed Jun. 6, 1994; and U.S. Ser. No. 96/035,40, filed Mar. 14, 1996.

Each of the publications, United States patents and United States patent applications cited herein are hereby incorporated by reference in this application.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of activating muscle cells to either stimulate or inhibit contraction thereof by applying electrical pulses thereto, wherein each pulse is applied for a duration in a range of about 10 to 500 milliseconds at a frequency in the range of about 0.05 to 5 Hz with a voltage in a range of about 0.1 to 30 volts and in trains of about 0.5 to 10 seconds.

2. The method of claim 1, wherein the muscle cells are muscle cells forming the wall of a uterus.

3. The method of claim 2, wherein the muscle cells are cells forming the wall of a cervix.

4. The method of claim 1, wherein the muscle cells comprise the wall of a human uterus.

5. The method of claim 4, wherein the human uterus is the uterus of a pregnant female.

6. The method of claim 5, wherein the electrical application is for stimulation of the uterus to contract and is applied with dosages of pharmacological agents selected from the group consisting of prostaglandins, antiprogestins and oxytocins.

7. The method of claim 5, wherein the application of electrical pulses inhibits the uterine contractility and is performed in the presence of pharmacological agents selected from the group consisting of nitric oxide, β-agonists, and steroid hormones.

8. The method of claim 4, wherein the human cervix is the cervix of a pregnant female.

9. The method of claim 5, wherein the electrical application is for stimulation of the cervix to contract and is applied with dosages of pharmacological agents selected from the group consisting of prostaglandins, antiprogestins and oxytocins.

10. The method of claim 5, wherein the application of electrical pulses inhibits the cervix contractility and is performed in the presence of pharmacological agents selected from the group consisting of nitric oxide, β-agonists, and steroid hormones.

11. The method of claim 1, wherein the electrical pulses are applied to an exposed wall of the muscle tissue.

12. The method of claim 1, wherein the electrical pulses are applied through electrodes on a needle embedded in the muscle tissue.

13. The method of claim 1, wherein each pulse is applied for about 100 milliseconds at a frequency of about 1 Hz with a voltage of about 10 volts and in trains of about 3 seconds.

14. The method of claim 2, wherein the nerves are nerves of a uterus or cervix.

15. A method of stimulating nerves which control smooth muscle tissue with muscle cells having a chronaxie in the range of about 0 to 100 milliseconds to cause the muscle tissue to either relax or contract comprising applying pulses thereto having a duration in a range of about 0.1 to 1 millisecond at a frequency of about 2.5 to 60 Hz with a voltage in the range of about 10 to 80 volts and in trains having a duration of less than 1 second to stimulate intramural nerve fiber.

16. The method of claim 14, wherein the nerves are nerves of a uterus or cervix.

17. The method of claim 16, wherein the uterus or cervix is a human uterus or cervix.

18. The method of claim 17, wherein the uterus or cervix is a uterus or cervix of a pregnant human.

19. The method of claim 15, wherein the electrical application is for stimulation of the uterus to contract and is applied with dosages of pharmacological agents selected from the group consisting of prostaglandins, antiprogestins and oxytocins.

20. The method of claim 15, wherein the application of electrical pulses inhibits the uterine contractility and is applied in the presence of pharmacological agents selected from the group consisting of nitric oxide, β-agonists, and steroid hormones.

21. The method of claim 17, wherein the human cervix is the cervix of a pregnant female.

22. The method of claim 17, wherein the electrical application is for stimulation of the cervix to contract and is applied with dosages of pharmacological agents selected from the group consisting of prostaglandins, antiprogestins and oxytocins.

23. The method of claim 17, wherein the application of electrical pulses inhibits the cervix contractility and is applied in the presence of pharmacological agents selected from the group consisting of nitric oxide, β-agonists, and steroid hormones.

24. The method of claim 16, wherein the uterus or cervix is a human uterus or cervix.

25. The method of claim 17, wherein the uterus or cervix is a uterus or cervix of a pregnant human.

26. The method of claim 24, wherein the human cervix is the cervix of a pregnant female.

27. The method of claim 24, wherein the electrical application is for stimulation of the cervix to contract and is applied with dosages of pharmagological agents selected from the group consisting of prostaglandins, antiprogestins and oxytocins.

28. The method of claim 24, wherein the application of electrical pulses inhibits the cervix contractility and is applied in the presence of pharmacological agents selected from the group consisting of nitric oxide, β-agonists and steroid hormones.

29. A method of stimulating nerves which control muscle tissue to cause the muscle tissue to either relax or contract comprising applying pulses thereto having a duration in a range of about 0.5 to 0.7 millisecond at a frequency of about 30 Hz with a voltage of about 30 volts and in trains in the range of about 1 to 3 seconds.

30. The method of claim 29, wherein the electrical application is for stimulation of the uterus to contract and is applied with dosages of pharmacological agents selected from the group consisting of prostaglandins, antiprogestins and oxytocins.

31. The method of claim 29, wherein the application of electrical pulses inhibits the uterine contractility and is applied in the presence of pharmacological agents selected from the group consisting of nitric oxide β-agonists and steroid hormones.

* * * * *